United States Patent [19]
Agrawal et al.

[11] Patent Number: 5,876,446
[45] Date of Patent: Mar. 2, 1999

[54] POROUS PROSTHESIS WITH BIODEGRADABLE MATERIAL IMPREGNATED INTERSTICIAL SPACES

[75] Inventors: C. Mauli Agrawal, San Antonio; Robert C. Schenck, Comfort, both of Tex.

[73] Assignee: Board of Regents, The University of Texas System, Austin, Tex.

[21] Appl. No.: 772,276

[22] Filed: Dec. 20, 1996

Related U.S. Application Data

[63] Continuation of Ser. No. 332,537, Oct. 31, 1994, abandoned.
[51] Int. Cl.$^6$ ........................................................ A61F 2/02
[52] U.S. Cl. .................................. 623/11; 623/16; 606/76
[58] Field of Search ............................ 623/11, 16; 606/76

[56] References Cited

U.S. PATENT DOCUMENTS

| | | | |
|---|---|---|---|
| 4,279,249 | 7/1981 | Vert et al. | 128/92 D |
| 4,563,489 | 1/1986 | Urist | 524/21 |
| 5,098,779 | 3/1992 | Kronzler et al. | 623/11 |
| 5,250,584 | 10/1993 | Ikada et al. | 623/16 |
| 5,258,029 | 11/1993 | Chu et al. | 623/16 |
| 5,263,986 | 11/1993 | Noiles et al. | 623/16 |
| 5,281,419 | 1/1994 | Tuan et al. | 623/16 |
| 5,522,895 | 6/1996 | Mikos | 623/16 |

FOREIGN PATENT DOCUMENTS

| | | |
|---|---|---|
| 0 194 192 | 9/1986 | European Pat. Off. . |
| 0361896A3 | 4/1990 | European Pat. Off. . |
| 0 550 875 A1 | 7/1993 | European Pat. Off. . |
| 0 636 377 A1 | 2/1995 | European Pat. Off. . |
| 2215209 | 9/1989 | United Kingdom . |
| 90/04982 | 5/1990 | WIPO . |
| 90/13302 | 11/1990 | WIPO . |

OTHER PUBLICATIONS

Albrektsson and Hansson, "An Ultrastructural Characterization of the Interface Between Bone and Sputtered Titanium or Stainless Steel Surfaces," *Biomaterials*, 7:201–205, 1986.

Aldinger et al., "Bone Morphogenetic Protein: A Review," *International Orthop. (SICOT)*, 15:169–177, 1991.

Bobyn, et al., "The Optimum Pore Size for the Fixation of Porous–Surfaced Metal Implants by the Ingrowth of Bone," *Clinical Orthopaedics and Related Research*, 150:263–270, 1980.

Buser et al., "Influence of surface characteristics on bone integration of titanium implants. A histomorphometric study in miniature pigs," *Journal of Biomedical Materials Research*, 25:889–902.

Cameron et al., "The Rate of Bone Ingrowth into Porous Meal," *J. Biomed. Mater. Res.*, 10:295–302, 1976.

Collier et al., "Bone Ingrowth into Dynamically Loaded Porous–Coated Intramedullary Nails," *J. Biomed. Mater. Res. Symposium*, 10(7):485–492.

Collier et al., "Macroscopic and Microscopic Evidence of Prosthetic Fixation with Porous–Coated Materials," *Clinical Orthopaedics and Related Research*, 235:173–180, 1988.

Cook et al., "Interface Mechanics and Bone Growth into Porous Co–Cr–Mo Alloy Implants," *Clinical Orthopaedics and Related Research*, 193:271–280.

D'Allessandro, J.S., et al., "Purification, Characterization, and Activity of Recombinant Human BMP–5," *Journal of Cellular Biochemistry*, Supplement 15F;166, 1991.

Ferguson et al., "Bovine Bone Morphogenetic Protein (bBMP) Fraction–induced Repair of Craniotomy Defects in the Rhesus Monkey (*Macaca speciosa*)," *Clinical Orthopaedics and Related Research*, 219:251–258, 1987.

Hulbert et al., "Attachment of Prostheses to the Musculoskeletal System by Tissue Ingrowth and Mechanical Interlocking," *J. Biomed. Mater. Res.*, 4:1–12, 1973.

Jansen et al., "Histologic evaluation of the osseous adaptation to titanium and hydroxyapatite–coated titanium implants," *Journal of Biomedical Materials Research*, 25:973–989, 1991.

Lindholm et al., "Bovine Bone Morphogenetic Protein (bBMP) Induced Repair of Skull Trephine Defects in Sheep," *Clinical Orthopaedics and Related Research*, 227:265–268, 1988.

Miller et al., "The Induction of Bone by an Osteogenic Protein and the Conduction of Bone by Porous Hydroxyapatite: A Laboratory Study in the Rabbit," *Plastic and Reconstructive Surgery*, 87(1):87–95, 1991.

Mizutani and Urist, "The Nature of Bone Morphogenetic Protein (BMP) Fractions Derived from Bovine Bone Matrix Gelatin," *Clinical Orthopaedics and Related Research*, 171:213–223,1982.

Ohgushi, et al., "Bone formation process in porous calcium carbonate and hydroxyapatite," *Journal of Biomedical Materials Research*, 26:885–895, 1992.

Sato et al., "Induced Regeneration of Calvaria by Bone Morphogenetic Protein (BMP) in Dogs," *Clinical Orthopaedics and Related Research*, 197:301–311, 1985.

Syftestad and Urist, "Bone Aging," *Clinical Orthopaedics and Related Research*, 162:288–297, 1982.

Takagi and Urist, "The Reaction of the Dura To Bone Morphogenetic Protein (BMP) in Repair of Skull Defects," *Ann. Surg.*, 196(1):100–109, 1982.

Urist et al., "Osteogenetic Competence," *Clinical Orthopaedics and Related Research*, 64:194–220, 1969.

Wlodarski and Reddi, "Importance of Skeletal Muscle Environment for Ectopic Bone Induction in Mice," *Folia Biol.*, 34:425–434, 1986.

Athanasiou et al., "Biodegradable Carriers of GF–$\beta$ in Rabbit Osteochondral Defects," 39th Annual Meeting, Orthopaedic Research Society, San Francisco, CA, Feb. 15–18, 1993.

Lind et al., "Transforming Growth Factor–$\beta$ Enhances Fracture Healing in Rabbit Tibiae," 39th Annual Meeting, Orthopaedic Research Society, San Francisco, CA, Feb. 15–18, 1993.

Lee et al., "Healing of Large Segmental Defects in Rat Femurs is Aided by RhBMP–2 Matrix," *J. Biomedical Materials Research*, 28:1149–1156, 1994.

*Primary Examiner*—Paul B. Prebilic
*Attorney, Agent, or Firm*—Arnold White & Durkee

[57] ABSTRACT

Medical devices, most particularly prosthesis, are defined having at least one porous tissue-mating surface. The tissue-mating surface of the device includes therein a biodegradable carrier, such as a biodegradable polymer. The pores or intersticial spaces of the tissue-mating surface of the device are impregnated with the biodegradable polymer. The prosthesis of the present invention provides for enhanced rigid fixation, as pores at the surface of said device provide for bony ingrowth as the biodegradable carrier, i.e., polymer, degrades. Methods for preparing said prosthesis are described. Methods for delivering a pharmacologically active substance by including a pharmacologically active substance in the biodegradable carrier (e.g., polymer) are also disclosed.

10 Claims, 3 Drawing Sheets

POROUS PROSTHESIS WITH BIODEGRADABLE MATERIAL IMPREGNATED INTERSTICIAL SPACES

This application is a file wrapper continuation application of Ser. No. 08/332,537, filed Oct. 31, 1994 now abandoned.

BACKGROUND OF THE INVENTION

1. Field of the Invention

The present invention relates generally to the field of prosthetic and orthopedic devices. More particularly, it concerns prosthetic devices having porous tissue-mating surfaces impregnated with a biodegradable material, such as a biodegradable polymer. The invention also relates to methods of preparing and using such devices.

2. Description of the Related Art

Every year many people require artificial hip, knee or shoulder implants (prostheses). Although such total joint prostheses have been in clinical use for decades, they are still plagued with problems associated with inadequate permanent, rigid fixation. Virtually all implants currently in use have a tendency to loosen with time, some to the extent of requiring revision.

There are two main techniques commonly used for fixation: cemented types using bone cement and uncemented or press-fit types. In cemented devices, a bone cement in common use is poly(-methyl methacrylate). This cement is applied in a dough-like state as a grouting agent between the bone and the implant. It flows around the contours of the bone and the implant and into the interstices of cancellous bone. Upon hardening, the cement forms a mechanical interlock between the bone and the implant. In effect, there is no bone in-growth linking bone and prosthesis when bone cement is used. Although bone cement gives good initial fixation, an increase in compliance often occurs due to formation of a soft tissue capsule over time. Thus, the absence of bone in-growth frequently leads to loosening of a bonecemented prosthesis.

Press-fit prostheses are not implanted with bone cement but rather into a prepared cavity in the bone which closely approximates the prosthetic shape; long term stability of such implants requires bone to form an interlock by growing into the prosthesis at the mating surface. Both porous and mesh type mating surfaces have been employed on press-fit prostheses to enhance fixation in bone, with various materials coated on the surfaces to allow desired bone growth.

Certain osteoconductive materials (e.g., hydroxyl-apatite applied by plasma-spraying) are favored for their durability and bonding strength, but obtaining the desired press-fit at surgery is often associated with problems (Geesink, R. G. T., *Clinical Orthopedics and Related Research*, 261:39–58 (1990)). Further, the cavity prepared in bone to receive the prosthesis is generally not optimally shaped, causing the actual bone contact achieved with insertion of the prosthesis to be only 10–20% of the potential mating surface. The remaining voids between bone and prosthesis, containing little or no osteoconductive material, decrease and/or impair the bone-prosthesis interlock necessary for long-term stability of the prosthesis.

Conventional press-fit prosthesis often provide inferior long-term fixation to bone because of inadequate and/or inconsistent bony in-growth. A porous surface on a prosthesis facilitates some minimal enhancement of bony in-growth. Thus, the overall use of a prosthesis with such a porous surface provides inferior long-term rigid fixation. A need remains in the medical arts for a press-fit device that achieves sufficient rigid fixation so as to be suitable for long-term prosthetic use.

The feasibility of achieving fixation of prostheses using bone in-growth is well established. However, studies have shown that clinically the bone in-growth is both inconsistent and inadequate (Collier et al. (1988), Clinical Orthopaedics and Related Research, 235:173–180). In a study of 226 retrieved porous-coated implants, Collier et al. determined that only 25% of femoral and 16 percent of acetabular components exhibited any significant bone in-growth. In an attempt to increase the degree of in-growth, some studies have successfully used rat marrow cells in HA implants in a rodent model (Ohgushi et al. (1992) J. Biomed. Mater., 26:885–895). Recently Miller et al. have described the use of an osteogenic protein in HA implants (Miller et al. (1991) Plas. Reconstr. Surg., 87:87–95). Implants with this protein showed a significant increase in the amount of bone in-growth compared to the controls of HA implants without the protein in a rabbit model. However, no mechanical testing of the interface was performed.

A protein with osteogenic properties was first identified in demineralized bone by Urist (Urist, M. R. (1965), Science, 150:893–895). This substance was termed bone morphogenetic protein (BMP) (Urist and Strates (1971), J. Dental Res., 50:1392–1406). BMP derived from human, bovine, and porcine sources has been shown to exhibit osteogenic activity in rats indicating that it is not species specific (Aldinger et al. (1991), International Orthop. (SICOT), 15:169–177). Because of the difficulty in isolating large amounts of purified BMP from bone, recombinant human proteins (BMP 2–5) have been expressed from a cDNA library prepared from the U2OS human osteosarcoma and other cell lines. Of these recombinant proteins, BMP2, 4, and 5 have been shown to maintain their osteogenic potential after purification (D'Alesandro et al. (1991), J. Cell. Biochem. 515F, p. 166).

The presence of exogenous osteogenic protein has been reported to enhance bone in-growth into a hydroxyapatite implant in a rat model (Miller et al. (1991) Plas. Reconstr. Surg., 87:87–95). U.S. Pat. No. 4,563,489 describes the combination of BMP and biodegradable polylacatic acid polymer that is implanted in viable tissue where the BMP is slowly released. However, the potential of using exogenous BMP at a bone surface to enhance bone in-growth or strengthen the bone-prosthesis interface at the surface of a bone prosthetic device has not been explored to any significant degree in the literature.

Another known protein that is osteogenic in nature is TGFβ (Joyce, M E, (1990), J. Cell Biol., 110:2197–2207; Noda, M. (1989), Endocrinology, 124:2991–2994). The use of this particular protein in enhancing fracture healing as a result of local application of exogenous TGFβ in adult animals is discussed in Lind et al. (1993, 39th Meeting, Orthopaedic Research Society, February, 1993, San Francisco, Calif.). Use of TGFβ, as well as other growth factors as a clinical tool in bone healing has also been proposed (Id.). Schakenraad et al. (Biomaterials, 9:116–20 (1988)), describe the development of a biodegradable hollow fiber of poly (l-lactide) for controlled release of contraceptive hormone.

A problem that exits in available drug or agent-treated prosthetic devices is that they typically release the drug or agent in relatively short, not therapeutically useful periods of time. This is due to at least two factors, (1) the immediate release of drug at an implant surface and (2) the relatively longer period of release necessary to provide therapeutic advantage. Thus, such devices are not particularly well suited for long term prosthetic implants.

The above review illustrates the need in the medical arts for prosthetic devices that enhance rigid fixation at prosthesis-tissue mating surfaces, and allow improved boney in-growth. Improved methods for controlling release of active agents at the surface of a press-fit prosthetic device over therapeutically useful periods of time are also needed.

SUMMARY OF THE INVENTION

The present invention seeks to overcome the above and other drawbacks inherent in the prior art, particularly those problems associated with long-term rigid fixation of a prosthetic device, by providing a medical appliance that enhances natural bio-fixation. Enhanced natural bio-fixation is achieved in part through the impregnation of at least one porous tissue-mating surface of a prosthetic device with a biodegradable composition. This biodegradable composition includes a biodegradable polymer or other matrix. This matrix may further include any variety of known therapeutic or pharmacologically active agents recognized by those of skill in the art, including growth factors and the like. Biodegradable materials that may be employed as part of the biodegradable composition include biodegradable ceramics and biodegradable polymers. By way of example and not limitation, such biodegradable polymers include PLA, PGA, various co-polymers of these polymers, and other biodegradable polymeric preparations. The impregnation of interstitial spaces with a biodegradable polymer on the surface of at least one tissue mating surface of an implantable device defines one particular feature of the claimed invention. In particular embodiments, the prosthetic device is a press-fit prosthetic device.

The devices and methods of the present invention go beyond the existing art by incorporating a biodegradable matrix within pores or crevices of at least one tissue-mating surface of an implantable device. This feature imparts the advantage of providing a mechanism whereby bone cell incorporation may be achieved gradually into the porous surface of the device as the polymer at the prosthesis surface degrades. Where a drug or other agent is included in the polymer, controlled release of the agent from the surface of the prosthetic device surface will also incidentally be achieved as the biodegradable matrix degrades.

The present devices may be used with virtually any tissue where enhanced prosthesis-tissue adhesion is desired. Use of the device as a bone prosthetic device in total joint and even dental applications constitute contemplated uses of the invention. These devices include at least one porous surface amenable to the incorporation of a biodegradable composition that comprises a biodegradable carrier or matrix material.

Virtually any prosthetic device or appliance that has at least one porous, in some aspects microporous, tissue mating surface may be employed in the practice of the present invention. There are a number of techniques that may be used to impart a porous nature to a surface. One such technique is to incorporate a multilayer beaded coating or mesh coating at the surface of the device. Where beads are layered onto a device to impart a porous characteristic to at least one tissue-mating surface of the device, the spheres or beads used will typically have a diameter of between about 250 and about 400 μm. These size beads produce surface pore intersticial spaces of between about 150 to about 250 μm. If the minimal internal interconnect diameter is at least 75–100 μm, bone tissue/cells will grow into the device at depths of 3–4 mm, although most coatings are thinner than this. Coatings of this sort may be fabricated from metals, polymers, and ceramics, although the most common combination is a cobalt-base coating on a cobalt-base alloy device.

An object of the present invention is to provide a device having an impregnated porous surface with a biodegradable porous interface between bone and surrounding tissues. A second object of the invention is to provide for the slow and controlled degradation of the biodegradable matrix over a prolonged period of time (weeks or months) that allows gradual growth of bone cells into the devices' surface matrices or intersticial spaces.

A further object of the present invention is to provide structures and methods of preparing structures (especially metallic) having at least one porous surface impregnated with a biodegradable composition, particularly biodegradable polymers. Still another object of the invention is to provide protracted degradation of a biodegradable polymer from an implanted device, and the use of this feature to achieve release of pharmacologically active agents at a bone-prostheses interface in vivo.

In one aspect, the prosthetic device of the present invention is described as having at least one porous tissue-mating surface impregnated with a biodegradable preparation, said biodegradable preparation comprising a biodegradable carrier material. More particularly, the biodegradable carrier in one aspect of the invention comprises a biodegradable polymer, such as a copolymer of about 50% polylactic and about 50% polyglycolic acid. The carrier material may optionally include a pharmacologically active substance or drug. Of course, any of a number of other biodegradable polymers may be used with equal efficacy. Additionally, polylactic acid alone may be employed to impregnate the surfaces of the invention. Polyglycolic acid alone may similarly be employed.

The particular polymer impregnated surfaces of the present device may be prepared on any variety of different shaped implantable prosthetic devices. For example, a porous tissue mating surface of a hip, knee, shoulder, elbow, ankle, wrist, hand, finger joint, temporal mandibular joint or dental implant, or acetabular cup may be treated according to the present invention to provide devices of improved rigid fixation to body tissues. It is anticipated that the most preferred embodiments of the device will be suitable for use as a total joint prosthesis, such as a hip, knee or shoulder prosthesis.

In a most preferred aspect of the present invention, a pharmacologically active substance or drug may optionally be included within the biodegradable carrier. By way of example, such a pharmacologically active substance is useful in the treatment of the body and capable of diffusing from a biodegradable carrier at a therapeutically effective rate. The term "drug" as used herein and is intended to be interpreted in its broadest sense as including any composition or substance that will produce a pharmacologic response either at the site of application or at a site remote therefrom.

Suitable drugs for use in therapy with the prosthetic devices and the drug-delivery system provided in embodiments of the invention that include them constitute, without limitation:

1. Anti-infective, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethazine, sulfadiazine, sulfamerazine, sulfamethizole and sulfisoxazole; antivirals, including idoxuridine; and other anti-infective including nitrofurazone and sodium propionate;

2. Anti-allergenics such as antazoline, methapyrilene, chlorpheniramine, pyrilamine and prophenpyridamine;
3. Anti-inflammatories such as hydrocortisone, cortisone, dexamethasone 21-phosphate, fluocinolone, triamcinolone, medrysone, prednisolone, prednisolone 21-phosphate, and prednisolone acetate;
4. Estrogens such as estrone, 17β-estradiol, ethinyl estradiol, and diethyl stilbestrol;
5. Progestational agents such as progesterone, 19-norprogesterone, norethindrone, megestrol, melengestrol, chlormadinone, ethisterone, medroxyprogesterone, norethynodrel and 17α-hydroxyprogesterone;
6. Humoral agents such as the prostaglandins, for example, $PGE_1$, $PGE_2$, and $PGF_2$;
7. Antipyretics such as aspirin, sodium salicylate, and salicylamide;
8. Nutritional agents such as essential amino acids and essential fats; and
9. Osteoinductive agents.

Other dregs having the same or different activity as those recited above can be employed in drug-delivery systems within the scope of the present invention.

Drugs can be in different forms, such as uncharged molecules, components of molecular complexes, or non-irritating, pharmacologically acceptable salts such as hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the drug-delivery device will vary depending on the particular drug used, the desired therapeutic effect, and the time-span over which drug delivery is desired. Since a variety of devices in a variety of sizes and shapes may be fashioned according to the present invention to include the drug/matrix coating, and which are intended to provide dosage regimes for therapy of a variety of maladies, there is no specific critical upper limit on the amount of drug incorporated in the device. The lower limit, too, will depend on the activity of the drug and the time span of its intended release from the device desired in a particular application. Thus, it is not practical to define a range for the therapeutically effective amount of the drug to include.

The treated or processed devices of the present invention may include prosthetic fittings for many different types of soft tissues, such as muscle and heart tissues, as well as bone tissues.

It is anticipated that the devices of the present invention adapted for use with a bone as a total joint prosthesis may be prepared from any variety of materials that have a tensile or mechanical strength sufficient to support a bone. By way of example, the prosthetic devices of the present invention may be prepared from metals or other high impact materials, such as a high impact, high molecular weight polymer or resin. The device includes at least one porous tissue mating surface. By way of example, the porous surface may comprise a cobalt chrome alloy, a titanium alloy or stainless steel.

Devices having a surface consisting of substances not amenable to the attachment or adhesion of a biodegradable composition containing a drug and a matrix material are not expected to be particularly useful in the practice of the present invention without modification or chemical treatment to enhance to an appreciable extent the adhesion of such a mixture. For example, a porous surface may be pretreated with a surfactant to enhance compatibility with such a mixture containing a biodegradable carrier, such as a biodegradable polymer. Devices having very smooth or non-porous surfaces are not expected to be particularly amenable to the incorporation of a polymer and drug mixture. However, devices having at least one textured or roughened surface with macroscopic surface space(s) that are amenable to the incorporation of a biodegradable matrix are expected to be amenable for use with the present invention.

Devices having plastic surfaces or polymer surfaces may also be used in conjunction with the present invention. For application to a plastic surface that is porous, the biodegradable composition will include a calcium sulfate carrier material, or other ceramic, with the drug or other agent of interest. This, and other ceramics that dissolve in water would be useful in such applications, as they will form a paste that will be capable of impregnating such a surface. Plastic and plastic-like porous surfaces may be treated or otherwise modified so as to satisfactorily bind or allow the attachment and incorporation of a biodegradable matrix material and drug composition. Such may be accomplished, for example, by machining the surface to create pores of crevices or a texture. Of course, the particular plastic of the device surface will dictate the choice of solvent(s) employed to prepare the biodegradable composition that is to be applied to the device surface.

In still another aspect of the invention, biodegradable compositions suitable for impregnating a porous (preferably micropores of between 75 μm to 400 μm size) surface of a prosthetic device comprising a pharmacologically active agent and a biodegradable carrier material are provided. In one embodiment, the carrier is a copolymer of polylactic and polyglycolic acids, most preferably in a mixture of about 50%/50% percent polylactic/polyglycolic acid preparation, and constitutes 15% (w/v) of the composition. Where trypsin inhibitor is the pharmacologically active agent, it is to be included within the mixture at a concentration of about 0.2 mg/ml. The daily dose in vivo provided from such a surface treated device will depend on the degradation properties of the polymer or carrier material selected, the relative porosity of the device surface, and the overall concentration of the drug or protein incorporated on the surface. The amount of polymer will also depend on the design of the particular prothesis. Additionally, the total amount of agent will depend on location of implant.

The present invention also provides methods for preparing porous surface devices having the aforedescribed biodegradable composition coating. A preferred embodiment of the method comprises preparing a composition of a biodegradable carrier having a consistency capable of impregnating pores of between about 75–400 μm, and treating at least one porous tissue-mating surface of the device with the composition a sufficient amount of time to allow the mixture to fill or impregnate at least one porous tissue-mating surface of the device.

Most preferably, the biodegradable carrier is a biodegradable polymer, such as an about 15% (w/w) solution of a 50%/50% polylactic and polyglycolic acid. However, any variety of other biodegradable polymers having a viscosity amenable to impregnating relatively small surface pores of a prosthetic device will be equally effacious for use in conjunction with the present invention. Generally, the biodegradable carriers, particularly polymers, should be of a suitable consistency and viscosity so as to allow for the substantially complete filling or impregnation of surface pores, such as pores of about 100–500 μm in size, most preferably pores of about 100–200 μm. Optimal bony-ingrowth is expected to be provided into prosthesis devices that include pores of approximately 250 to 500 microns.

Insofar as the present invention may include pharmacologically active substances, the invention also provides methods for the delivery of a drug in vivo. These methods comprise in one embodiment implanting a prosthetic device having at least one porous tissue-mating surface impregnated with a composition of a biodegradable carrier and the drug to be delivered. In one embodiment, the biodegradable carrier is a polymer, most preferably a copolymer of about 50% polylactic acid and about 50% polyglycolic acid, together with BMP. However, other biodegradable carriers and drugs may be used in conjunction with the present invention with equal efficacy, such as those enumerated in Table 1.

The present invention also provides a method for preparing a prosthesis suitable for the delivery of a drug in vivo. In one preferred aspect, the method comprises preparing a biodegradable preparation comprising a drug and a biodegradable carrier and treating at least one porous tissue-mating surface of the prosthesis with the biodegradable preparation a sufficient amount of time to allow the preparation to fill the porous tissue-mating surface of the prosthesis. Most preferably, the tissue-mating surfaces of the prosthetic device are comprised of a titanium or cobalt chrome alloy, or stainless steel. In a preferred embodiment, the porous tissue (bone) mating surface of the prosthetic device is comprised of metallic beads. Alternatively, the device may be fashioned so as to include at least one tissue (bone) mating surface that is formed from a series of metallic threads, thereby also creating pores or interstices at the surface of the device.

A typical example of a treated bone prosthesis would include a prosthetic stem having at least one porous bone-mating surface that is impregnated with a biodegradable carrier. The biodegradable carrier may optionally include a drug, such as BMP or growth hormone. In another embodiment of the prosthesis, the porous tissue (more particularly, bone)-mating surface is provided onto the surface of a device with a number of metal beads incorporated onto at least one tissue-mating surface of the device. Alternatively, the porous tissue-mating surface may be comprised of a series of metal threads, such as a metal mesh or screen, or a ceramic.

Biodegradable materials that may function as carriers of a drug or other pharmacologically active substance as defined in the present invention, are in particular aspects of a polymeric or a ceramic strength. Bone growth factors in drugs may be readily incorporated into such materials. By way of example, proteins that are osteogenic in nature may be used in conjunction with the claimed biodegradable composition-impregnated prosthetic devices.

The enhanced rigid fixation from the growth of bone cells into the device to replace the pores within the porous bone mating surfaces provides an enhanced rigid fixation of said prosthesis not previously provided by other uses of porous prosthesis or techniques which employ cementing fixation.

In order to be useful in conjunction with the biodegradable polymer preparation, the prosthetic device should include at least one porous surface that mates against a bone or tissue. A porous surface, by way of example, may be achieved though including a mesh or mesh-like covering to the device, a series of beads, or a surface otherwise treated to include a roughened or "pocked" surface. Most preferably, the porous surface will encompass at least that area on the device that is necessary for tissue— (e.g., bone) prosthesis contact. The device surface to be treated for optimal tissue in-growth and rigid fixation will depend on the anatomic site of insertion, as known to those of skill in the art. It is not required that the entire surface or even all tissue or bone mating surfaces of the prosthesis be porous, but only that a sufficient part of the surface be porous so as to provide at least one tissue-contact surface that provides stable fixation in the body. For example, where the prosthesis is a total hip prosthesis, the medial surfaces and inner aspect of the proximal third of the device are preferably treated with the herein disclosed porous drug-carrier coating to provide satisfactory rigid fixation of the device. In fact, one would preferably not typically include a porous drug treated feature to the distal stem of such a device, as such would in some cases actually decrease the overall stability of the prosthesis by promoting or enhancing undesirable mechanical loading on the implanted device. Previous experience in total hip replacement or total hip arthroplasty has revealed that distal femoral stem bony ingrowth results in stress protection of the proximal segment resulting in proximal femoral body resorption, and implant fixation failure (that is, the implant loosens).

By way of example, biodegradable carriers or matrices that may be used to incorporate a pharmacologically active substance or drug to a porous prosthesis tissue-mating surface include the biodegradable polymers and ceramics. By way of example, such polymers include: PLA-PGA copolymer, PLA, poly caprolactone, polyanhydrides, gelatin, and hydroxymethyl cellulose. Commercial sources for these materials are well known to those of skill in the art, such as Birmingham Polymers, Inc. (Birmingham, Ala.), Medisorb, Boehinger-Ingleheim; Sigma, and Aldrich Chemical Company.

The term "biomaterial," as it applies to the present invention, is used to particularly include materials which are osteoconductive (comprising a scaffold or surface suitable for bone growth) or osteoinductive (promoting differentiation of pluripotential mesenchymal cells into osteoblasts). Biomaterials that are neither osteoconductive or osteoinductive, but merely bioinert or biodegradable materials which act to convey other biomaterials which are osteoinductive (e.g., osteogenic proteins), are also properly included as "biomaterial". Such substances may also be used in conjunction with the present invention.

Biodegradable materials comprise materials which are separated or chemically altered by natural processes within the body to yield substantially non-toxic degradation products. Such materials include, for example, the biodegradable polymers PLA and PGA. A bone growth factor is any substance that is required for or that enhances growth of bone.

Bone morphogenetic protein is an osteoconductive protein having biological properties and chemical characteristics well characterized in the art. For example, BMP is available from Genentech and is described in Takagi and Urist (1982)[19], which reference is specifically incorporated herein in its entirety for this purpose. The Merck Index (11th edition, (1989), Merck & Co., Inc. publishers) also includes information regarding the chemical characteristics of a variety of other biologically active substances that may be used together in a biodegradable matrix in preparing the claimed surface-treated devices. The Merck Index is specifically incorporated herein in relevant part, insofar as additional characterizing information about significant chemicals, drugs, and biological substances in the monograph section of this reference may be used in the practice of various embodiments of the present invention. Specific information regarding alternative chemical names for a drug, molecular formulas, molecular weight, biological, pharmacological and clinical information, chemical structures, toxicity data, physical data and therapeutic category is provided as part of the referenced Index.

Given the art recognized biological activities of BMP, it is within the ordinary skill of one in the art to formulate this agent to be used in the practice and formulation of this agent with a polymer. Once formulated in a polymer or other biodegradable carrier, the composition would then be used to impregnate or fill up the interstitial spaces on the surface of a prosthetic device. Generally, one would not employ fabrication steps that expose BMP or any protein drug to temperatures in excess of 37° C. for any extended period of time, as such is known to those of skill in the art in most cases to reduce or destroy biological or pharmacological activity. Thus, care should be taken to employ formulation protocols (temperatures, pH, etc.) that will substantially preserve (i.e., not reduce more than 50%), or at least not destroy significantly, the recognized pharmacological activity of the drug or other agent employed.

General techniques that may be used in the fabrication of compositions of a biodegradable material and a drug are outlined in Remingtons Pharmaceutical Sciences (1990), 18th edition, Mack Publishing Co., parts 2, 4, 6, 8), which reference is also specifically incorporated herein by reference in pertinent part for this purpose.

Generally, the polymer of choice may be employed in conjunction with any variety of solvents, such as acetone, methylene chloride or chloroform. The particular solvent to be used will be determined in part by the polymer selected. Most preferably, where PGA/PLA polymer is used, the solvent of choice is acetone.

As used in the description of the present invention, the term "microporous" is defined as pores having a size of between about 50 $\mu$m and about 600 $\mu$m, and most preferably between 100 $\mu$m to about 500 $\mu$m. In a most preferred embodiment, the term microporous is intended to define a pore size at a tissue-mating surface of a device of about 400 $\mu$m. This term is used to define more particularly the pores of a tissue-mating surface of a prosthetic device that is amenable to being impregnated with the biodegradable composition described herein. The device itself need not be porous throughout, but must at least include a surface that includes pores of the type described herein.

The terms "mesh" and "mesh type" in the present application refer to tissue-mating surfaces of a prosthesis having a fine woven character resembling a mesh with interstitial spaces sufficiently large to allow the passage through the mesh of particles up to about 400 $\mu$m maximum dimension, but preferably no larger. The term mesh is also used to define surfaces that instead include a series or coating or coatings of beads or ball-like structure so as to render a porous character to at least one tissue-making surface or part of such a surface on the desired prosthetic device. The pore size is most preferably of a sufficiently small pore size to allow for the optimal attachment and/or anchorage and ingrowth of tissue cells (e.g., bone cells) into the surface pores of the device, and of a sufficiently large size so as to provide a gap size sufficient to incorporate (i.e., become impregnated with) useful quantities of the biodegradable carrier (e.g., polymer) and drug mixture.

The term "self-sealing" applies to bone mating surfaces of the device designed as to allow the escape of osteoconductive and bioactive materials from the surfaces of the device.

The term "mating surface" used to describe the present invention refers to the surface of a prosthesis that is normally in contact with a tissue in its intended implanted site in the body. For example, where the prosthesis is a bone prosthesis, the device will include a surface that mates against a bone tissue. In contrast, where the device is intended for cardiac application, the mating surface is more accurately defined as a soft (heart or artery) tissue mating surface. "Non-mating" surface is any prosthetic device surface which is not a "mating surface", i.e., a surface of the device that is not substantially in contact with a bone or other tissue surface implanted at an intended site in vivo.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A is a side view diagram of press-fit prosthesis 1 having a porous bone-mating surface as emplaced in a bone 6. Box 7 in FIG. 1A identifies porous tissue-mating surface of prothesis 4 that contacts the bone surface 6; FIG. 1B—Diagrammatic cross section representation of porous bone-mating surface 4. The porous bone mating surface of the prosthesis includes a porous surface 7. The pores or voids of the surface are impregnated with a biodegradable composition 9. This composition most preferably includes a mixture of a pharmacologically active ingredient such as an osteoinductive material (e.g., bone morphogenic protein) or drug and a biodegradable polymer or ceramic. Arrows 11 depict the release of the osteoinductive material or drug from the treated porous bone-mating surface 4 of the device 1, and out onto the bone surface 6 that the bone prosthesis is mated against.

FIG. 2A is such a microscopic view of a porous (microporous) surface taken before treatment with a biodegradable composition of trypsin inhibitor and PLA/PGA polymer carrier. FIG. 2B—Microscopic view of the porous bone mating surface of the device after treatment with a biodegradable composite. FIGS. 2A and 2B demonstrate pores 13 after treatment with biodegradable composite of 50%/50% PLA/PGA copolymer and trypsin inhibitor protein.

DETAILED DESCRIPTION OF THE PREFERRED EMBODIMENTS

The porous surface prosthetic devices impregnated with a biodegradable composition of the present invention provide an improved medical device with enhanced tissue, particularly bone, fixation rigidity. The inclusion of bioactive substances in a biodegradable carrier or matrix at tissue-mating porous surfaces the device, further promotes the ingrowth of cells, such as bone cells (osteoblasts) into the porous surface of the device and into the voids created by the gradual biodegradation of a biodegradable carrier. The porous nature of the device's tissue-mating surfaces encourages and supports enhanced growth and attachment of tissue cells by providing a more amenable surface for the growth and attachment of anchorage dependent cells, such as bone cells. Enhanced rigid fixation of such treated devices in the body is thus also achieved.

A biodegradable substance that is employed as the biodegradable matrix or carrier may be described as a biodegradable polymer, ceramic or mineral. Examples of preferred biodegradable materials that may be used as such carriers or matrixes include polylactic acid, polyglycolic acid, polycaprolactone, polyanhydrides and polyorthoesters, as well as co-polymers thereof.

Direct apposition of the tissue (such as bone) to the impregnated pores or mesh of the present prosthetic devices encourages improved tissue ingrowth as matrix filling the porous surfaces of the prosthesis degrades, the biodegradable material within the pores are replaced by the host's tissue cells (e.g., bone). Tissue (bone) will subsequently occupy available spaces on the prosthesis tissue-mating surfaces to provide enhanced rigid fixation.

Figure 1A:
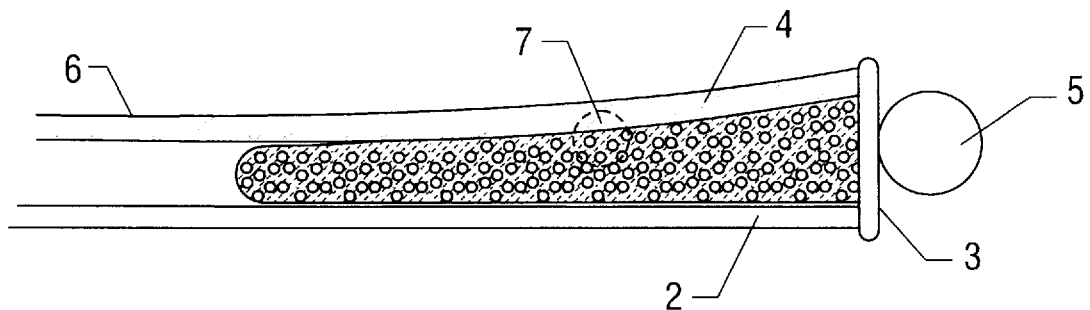
FIG. 1A and FIG. 1B provide schematic views of the prosthetic device

A preferred embodiment of the present invention is illustrated in FIG. 1A. The prosthesis 1 is press-fit into the bone 6, the bone prosthesis interface being at surface 4. FIG. 1A shows a schematic representation of a side view of the prosthetic device implanted into a bone 6, such as an femoral prosthesis emplaced in a human thigh bone. A biodegradable composition, comprising a biodegradable matrix or carrier, is impregnated in the pores as a biodegradable matrix 9 (see FIG. 1B) sufficiently to fill the pores of such a surface prior to implantation. At least one porous tissue mating surface of the device is treated.

Figure 1B:
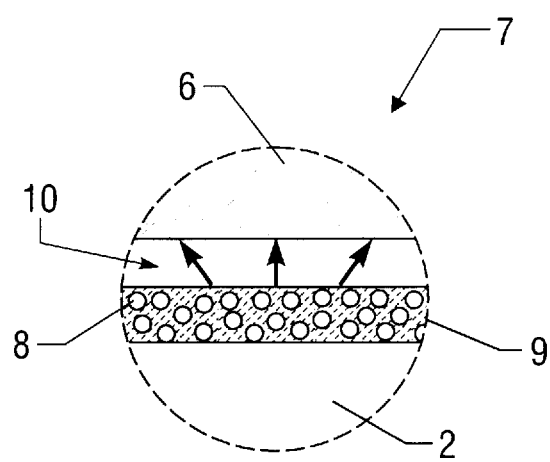

Box 7 in FIG. 1A identifies the porous tissue mating surface of prothesis 1 that interfaces at bone-prosthesis interface 4. FIG. 1B illustrates a detailed cross-section of the prosthesis porous tissue-mating surface 4 in conjunction with a tissue (e.g. bone) surface 6. Pores on the surface of a device that are amenable to impregnation or filling with a biodegradable composition may be created by covering a surface of the device with tiny beads or spheres 8. The pores of the prosthesis bone-mating surface are impregnated (filled) with a biogradable composition 9 creating a biodegradable matrix between the beads or spheres. The composition may further include a pharmacologically active substance. Arrows 10 depict the release of a pharmacologically active substance or drug material from the biodegradable matrix of the composition 9 from the tissue mating surface 4 of the device 1, and out onto the bone or other tissue surface 6 that it is mated against.

Figure 2A:
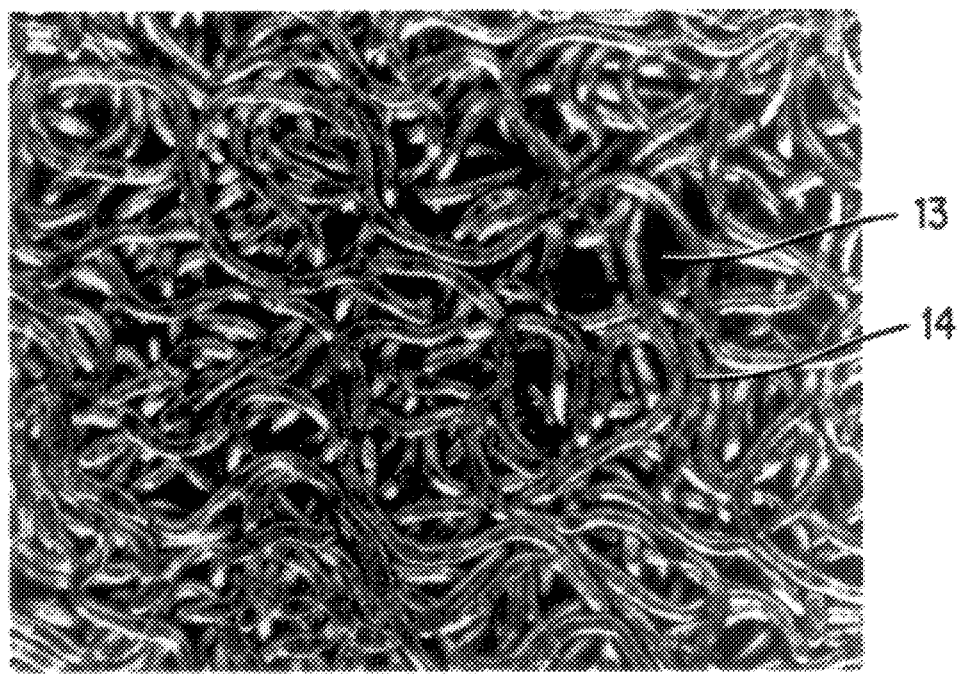
FIGS. 2A and 2B present microscopic views of the porous bone-mating surface of the device.
Figure 2B:
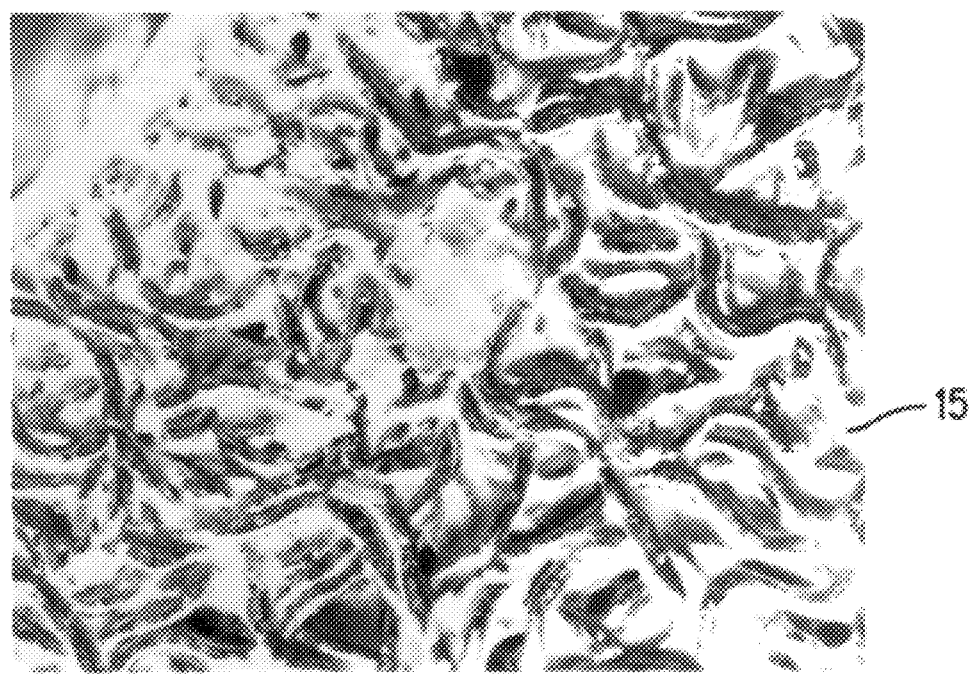

FIG. 2A is a microscopic picture of a porous tissue mating surface of the prosthesis before treatment with a biodegradable composition. Areas 14 are created by the raised surfaces of the beads, mesh or screen at the surface of the prosthesis. Areas 13 are pores or depressions created between the raised areas 14. Upon treatment with a biodegradable composition of the biodegradable matrix (polymer) and a drug as described herein, the pores 13 of the tissue mating surface of the device become filled with the biodegradable composition, as depicted in FIG. 2B, areas 15. The biodegradable composition used in the device from which these photographs were taken was a 50%/50% PLA/PGA copolymer biodegradable matrix material, and trypsin inhibitor protein. Of course, the particular substance or drug release characteristics of the treated surfaces may be designed into the device by the selection of either rapidly or more slowly biodegradable polymers or other carrier, or by the addition of substances to the carrier material that either increase (e.g., enzyme) or decrease (i.e., higher molecular weight polymers or resins) the rate at which the carrier is broken down in the body. The degradation rate, and hence drug release rate, may also be controlled by the molecular weight of the polymer used as matrix, as well as the pharmacologically active agent incorporated.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Fabrication of a Prosthesis with a Porous-Tissue Mating Surface Impregnated with a Biodegradable Composition The present example is provided to demonstrate the utility of the present invention for the preparation of bone prosthetic devices that have surfaces with enhanced biocompatibility and enhanced bio-fixation activity.

The substance used together with the biodegradable carrier in the present example is a protein known as trypsin inhibitor. This protein exemplifies the utility of the present invention with other proteins as part of a biodegradable matrix.

Known growth factors that may be useful in the practice of the present invention are TGFβ and BMP. Both naturally occurring (i.e., tissue derived) and recombinant forms of these substances may be used in the practice of the present invention with equal expected efficacy.

Formulation of Biodegradable Composite with Osteoinductive Substances

Trypsin inhibitor was chosen as an exemplary protein because it is known to have many properties in common with an osteoinductive protein known as a bone morphogenetic protein (BMP). Thus, one of skill in the art would expect that the release characteristics of BMP would be similar to those of trypsin inhibitor as part of a similar biodegradable composition. The common characteristics between TI and BMP include:

1. Comparable molecular weight: (about 18 kD),
2. Similar hydrophobicity, and
3. Drug release characteristics.

Figure 3:
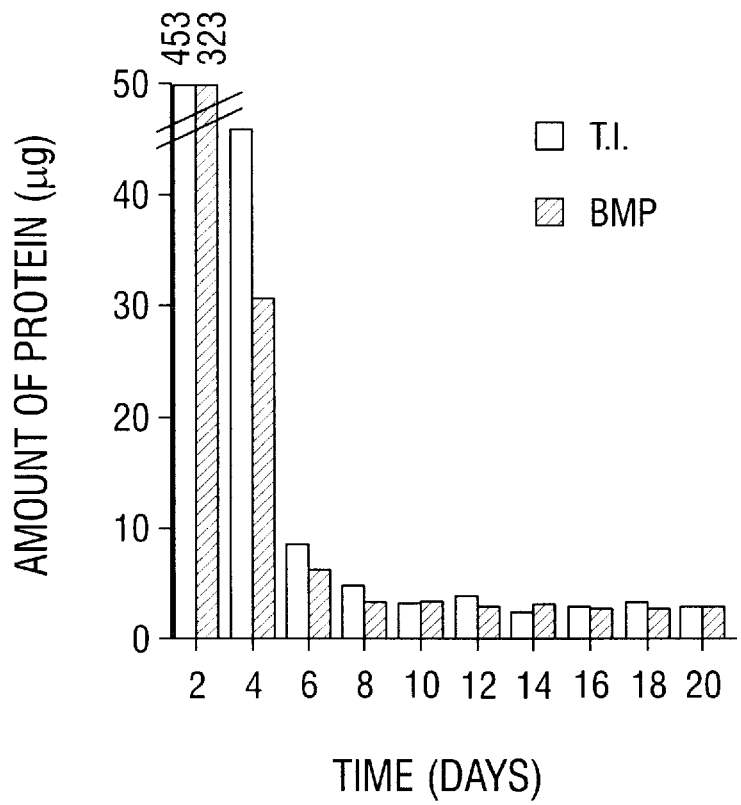
FIG. 3—Graph showing similarity of release of BMP and trypsin inhibitor from a biodegradable implant fabricated from 50:50 PLA-PGA material. This graph shows that TI is a representative model protein to study release characteristics from a biodegradable polymeric matrix.
Figure 4:
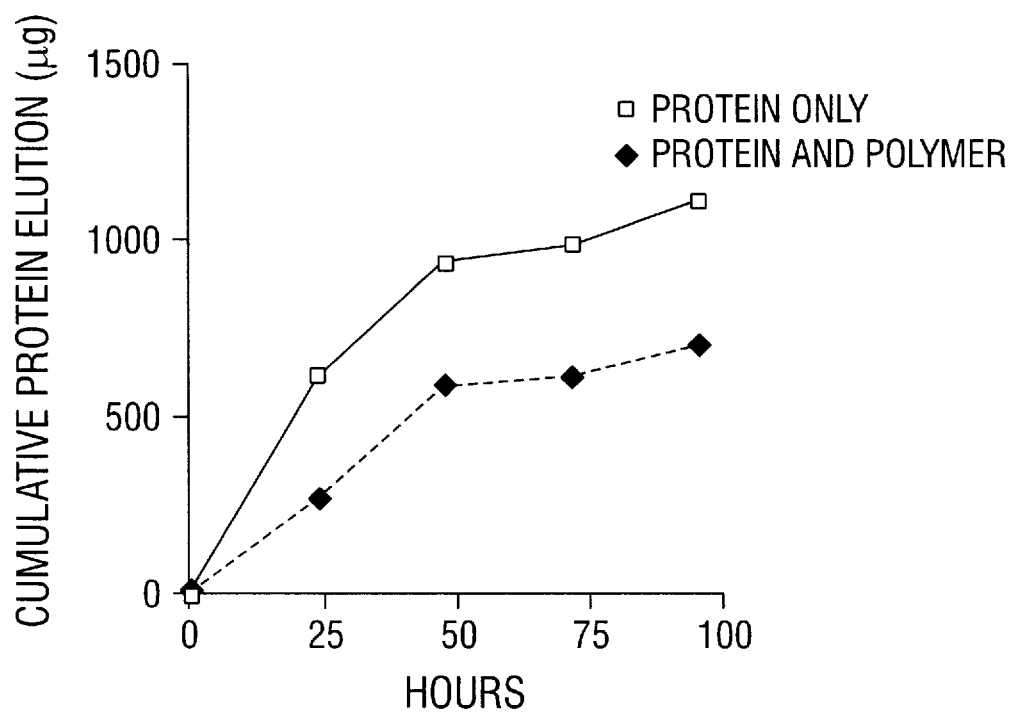
FIG. 4—Graph showing a comparison of protein (trypsin inhibitor) release from a porous implant surface coated with protein alone (-■-) or coated with a polymer and protein mixture (-●-) of trypsin inhibitor in a 50:50% PLA:PGA polymer the release kinetics demonstrate a characteristic burst release effect within 25 hours of devices coated with protein alone. The protein and polymer mixture demonstrates a slower more controlled protein release over the first 50 hours.

The drug release characteristics of these two proteins (BMP and TI) from a biodegradable matrix of PLA-PGA are very similar as indicated in FIG. 3.

In the present example, trypsin inhibitor (TI) was obtained from Sigma Chemicals (Lot 40 H8200). The carrier matrix (a 50%/50% copolymer of PLA-PGA) was used to impregnate a mesh-covered prosthetic devise.

The following material were used in the present composite:

(i) Copolymer of polylactic and polyglycolic acids (Birmingham Polymers, Inc., Birmingham, Ala.);
(ii) Trypsin inhibitor (TI) as a substitute protein.

The following two techniques were used for incorporating the biodegradable composition of TI and PLA/PGA in the surface pores of a prosthesis.

Technique 1-GEL

A 15% (w/v) solution of a 50%–50% PLA-PGA copolymer was prepared in 5 ml of acetone at 45° C. Approximately 1 mg of TI powder was stirred into this solution to obtain a uniform suspension. This mixture was then pored into the pores of the prosthesis, which was then covered with a glass lid. It was allowed to stand for 24 hours whereupon the polymeric solution formed a gel. The prosthesis is then immersed in a 2:1 mixture of acetone and ethanol for about 24 hours. This process is repeated in 1:1 and 1:2 acetone-ethanol mixtures. Finally, the prosthesis is immersed in distilled water for 12 hours followed by air drying.

Technique 2-Gel

A 15% (w/v) solution of 50%–50% PLA-PGA copolymer was prepared in 5 ml of acetone and 1 mg of TI was incorporated in this solution. Low heat is provided to maintain a temperature of 35–40° C. One milligram of TI is added to this solution for every 5 ml of acetone and stirred to obtain an even suspension. This mixture is then poured into the pores of the prosthesis, covered with a glass plate and allowed to stand for 24 hours. The polymeric solution forms a gel. The mixture (T1+PLA/PGA) was then pored into the pores of the prosthesis as described above.

In this technique, the prosthesis was left uncovered and the acetone allowed to evaporate leaving behind a precipitate of the polymer-TI mixture in the pores. Further high vacuum treatment of the implant at low heat ensured full removal of the acetone. FIG. 2 shows the details of the polymer-protein impregnated structure.

Technique 3—Layering

A 40 percent (w/v) solution of 50:50 PLA-PGA copolymer is made in acetone. A vortex is used to ensure that the polymer is fully dissolved and a uniform solution is obtained. This is known as solution A. A separate solution/suspension of TI (trypsin inhibitor) is prepared in ultra-pure water. Approximately 5 mg of protein, in this case trypsin inhibitor, is added per 1 ml of water. This is known as solution B.

Step 1: Using a syringe, a known amount (depending on size of prosthesis) of solution A is added to the pores of the porous coated prosthesis. The prosthesis/implant is then allowed to air dry for 20 minutes followed by vacuum treatment for 20 minutes. This process allows the solvent (acetone) to evaporate leaving behind a layer of polymer in the pores of the prosthesis.

Step 2: Next, a known amount (depending on size of prosthesis) of solution B is added to the pores. As before, the prosthesis/implant is then allowed to air dry for 20 minutes followed by vacuum treatment for 20 minutes. This allows the water to evaporate leaving behind a layer of protein, in this case trypsin inhibitor, on top of the polymer layer.

Steps 1 and 2 are then repeated until the desired dose/concentration of the protein, in this case trypsin inhibitor, is incorporated in the prosthesis or implant. It is desirable that the last step is Step 2.

The above materials are only exemplary of this technique. Different biodegradable polymers and proteins can also be used by one of ordinary skill in the practice of the present invention.

The above three techniques are only exemplary of the possible methods and materials that can be used to fabricate and incorporate a biodegradable composition into a porous tissue mating surface of a prosthesis.

EXAMPLE 2

Preparation of Porous Surface with Biodegradable Composite of Bone Morphogenetic Protein on a Total Joint Prosthesis The present prophetic example is provided to outline one particular method for incorporating a pharmacologically active agent, such as BMP, and polymer mixture into the pores of a prosthetic device. A biodegradable composition of 50% PLA/50% PGA biodegradable carrier and bone morphogenetic protein is described in the present example.

The technique described in example 1 for formulating a biodegradable composition of BMP and PLA/PGA (concentrations of the drug, percentage of PLA to PGA, length of treatment of mesh surface of a prosthesis) may be employed. The difference in the procedure will include incorporating lesser amounts of the BMP than was used for trypsin inhibitor.

Alternatively, the polymer could be injected into the implant after the implant has been inserted to avoid interference with the mechanical fixation of the implant, although one could pretreat the surface with matrix/drug as described herein. In still other aspects, the implant may be first fixed in the bone space and then the matrix/drug injected into the implant, thus allowing flow of the matrix composite to the porous surface.

EXAMPLE 3

Prosthesis with Biodegradable Composite of Other Polymers

The present example is provided to illustrate the preparation of biodegradable compositions suitable for use in impregnating a porous surface of a prosthetic device with a variety of polymers. The particular polymer illustrated in this example is polycaprolactone (PCL). This polymer was obtained from Birmingham Polymers, Birmingham, Ala.

Generally, biodegradable polymers of a relatively low molecular weight are most preferred in preparing polymer and drug compositions. For example, biodegradable polymers having a molecular weight of less than about 100,000 kDa are preferred, with polymers having a molecular weight of between about 40 kDa and about 100,000 kDa being most particularly preferred. Of course, the prosthetic device surface may be comprised of a higher molecular weight polymer or resin, characteristic of materials with high impact resistance.

Alternatively, the polymer may comprise a mixture of different biodegradable or partially biodegradable polymers. An exemplary list of the most preferred polymers is provided in Table 1.

TABLE 1

| Polymer | Source |
| --- | --- |
| PGA | BPI |
| PLA | BPI |
| Polycaprolactone | BPI |
| Polyanhydride | BPI |
| Gelatin | Sigma |
| Hydroxy methyl cellulose | Sigma |

Polycaprolactone

By way of example, the polymer polycaprolacatone (PCL) may be dissolved in a quantity of methylene chloride so as to achieve a 15% (W/V) solution. Preferably, the methylene chloride is heated up to 40° C. if needed to facilitate dissolution of PCL in the solvent. An appropriate amount of bone morphogenetic protein (BMP) would then be stirred in to obtain a uniform suspension of about 2 µg BMP/ml polymer solution, or other therapeutically useful concentration. Optimally, the device surface will include a total dose of 0.5 mg BMP after impregnation with the biodegradable matrix.

The liquid suspension would then be poured onto at least one porous tissue-mating surface of a prosthetic device, such as a hip joint prosthesis, the porous surface being provided by a matrix of pores on the surface of the device, such as that created by affixing metallic beads or threads, to at least one tissue-mating surface of the device.

Polyanhydrides

The same technique described above may be used with equal efficacy with polyanhydrides as the matrix material.

The device will then be processed through several stages of phase exchange using a mixture of acetone, methanol, and water to obtain a microporous polymer-BMP solid matrix in the pores.

Alternatively, the prosthesis may be left uncovered and the acetone allowed to evaporate, leaving behind a precipitate of the polymer-BMP mixture in the pores. A high vacuum treatment at low heat (less than about 37° C.) of the implant may also be included for a sufficient amount of time to ensure full removal of acetone, or other solvent, used in the process.

Plastic of Paris ($CaSO^4$ $H_2O$)

Add water to powder to obtain a paste. The protein is then added to the paste and mixed in evenly. The paste is then used to fill the pores of the prosthesis.

EXAMPLE 4

In Vivo use of with Biodegradable Composition Impregnated Surface Prosthesis The present example defines one particular embodiment of the claimed devices for use as an in vivo bone prosthesis. Techniques for determining the release kinetics of a particular pharmaceutically useful agent in vivo from a device prepared according to the present invention are also proposed.

Biomaterials

The biomaterials to be used in vivo include preferably prosthetic devices having at least one tissue mating microporous surface. Untreated devices (i.e., no biodegradable polymer+microporous surface) are commercially available. These devices include surfaces made of a titanium alloy (Ti6A14V), with a porous surface (sintered beads), and sintered hydroxyapatite with a pore size range of 100–200 µm (Biointerfaces, San Diego, Calif.).

Rectangular specimens of size 3×3×15 mm will be used for the rabbit model described herein. These specimens will be degreased using Micro® laboratory cleaning solution and ultrasonically cleaned in acetone, methanol and distilled water. In addition, the titanium specimens will be pacified in 30% nitric acid. The specimens will then be sterilized by autoclaving at 140° C. for 90 minutes.

Surface Characterization

The surface of a representative number of samples of each type will be characterized using the following criteria:

Chemistry

In terms of bone bonding, the uppermost atom layers of a biomaterial surface are of paramount importance because it is these layers which either facilitate or discourage interatomic bone-biomaterial bonding. Accordingly, scanning Auger electron spectroscopy (AES) will be used to characterize spatially (relative to microstructure) and semi-quantitatively, the chemical species within the first few nanometers of the sample surface. Auger analysis of non-conductors like HA is difficult. However, the inventor has previously achieved good results by minimizing specimen current (typically less than 10 nA) and specimen thickness (below 0.5 mm). Loss of ions due to beam sputtering of the specimen will be avoided by a real rastering rather than local "point" scanning. A Physical Electronics Model 595 Auger spectrometer is available for this task.

Surface Morphology

The overall surface topography and the average pore size for each biomaterial will be determined by scanning electron microscopy (SEM) using a JOEL JSM 840A SEM. Non-conducting samples will be coated for the SEM study with a 50–100 A thick conducting layer of gold-palladium prior to viewing.

Incorporation of Biodegradable Polymer and drug; in vitro release kinetics

To incorporate BMP in the porous biomaterials, the technique described herein will be used. BMP will be used as the model protein because it is readily available and its activity in vivo and in vitro has been thoroughly described. For each implant, 15% (w/v) solution of 50%–50% PLA-PGA copolymer will be prepared in acetone and 50 ng of BMP will be incorporated in this solution. The mixture will then be poured into the pores of the implant. The implant will be left uncovered and the acetone allowed to evaporate leaving behind a precipitate of the polymer-BMP mixture in the pores. Further high vacuum treatment of the implant at low heat (<37° C.) will ensure full removal of the acetone. The methodology is designed to minimize the loss of BMP and simultaneously maximize the removal of all organic solvents.

Six specimens of each biomaterial will be tested to evaluate the in vitro kinetics of BMP release from the implants. After the incorporation of BMP and copolymer in their pores, the specimens will be weighed and then immersed in 20 ml of phosphate buffered saline (PBS), pH 7.0, at 37° C. in separate vials. Every three days a sample of the PBS will be obtained from each vial and analyzed for BMP content as a function of time using a MicroBCA assay. To maintain the neutral pH, the PBS in the vials will be changed every three days after obtaining the samples for analysis. The study will be performed for 56 days.

Recently some studies have questioned the long term biocompatibility of the family of polylactic and polyglycolic acids (Bab et al. (1985) Calcif. Tiss. Int., 37:551–555; Amir et al. (1989) Biomaterials, 10:585–589). However, these studies used large quantities of the materials in vivo, and detected problems only after an average of 4 months post-surgery. In the presently proposed study, only small quantities of a low molecular weight copolymer will be implanted and it is expected that it will bioabsorb in 8 weeks in vivo without any complications.

EXAMPLE 5

Clinical Applications of a Bone Prosthesis having a Microporous Polymer-Impregnated Surface The present example is provided to outline a most preferred proposed use of the claimed prosthetic devices as bone prosthesis (a press-fit prosthetic device), and particularly for th release at a bone-prosthesis interface of a drug within a polymer. Most preferably, the prosthesis is contemplated for use in humans.

Considerations including patient positioning and closeness of the press fit govern where the prosthesis should be located in each case. In every case, the biodegradable composition is to be used to impregnate at least one porous (microporous) bone-mating surface of a prosthesis so as to form an osteoconductive interface with the bone (FIG. 1B).

For delivery of BMP at a bone-prosthesis interface, a bone prosthesis useful for a thigh replacement prosthesis having at least one porous bone-mating surface would be treated with a biodegradable mixture of 50% PLA/50%PGA and 0.2 mg/ml BMP. Upon sufficient drying of the matrix (i.e., evaporation of polymer solvent), the device would be sealed in sterile fashion until use. Prior to insertion of the device prosthesis, the patient site of implant would be prepared to accommodate the prosthesis.

The prosthesis would then be removed from its sterile environment and then inserted into the patient using techniques well known to those of skill in the surgical arts. The general steps for accomplishing insertion of the prosthesis are as follows:

1) Exposure of the specific joint with dislocation according to standard and accepted tissue planes.
2) Formation of a bony cavity to allow optimal mechanical fixation of the implant to bone. Details include cutting of bone ends and excision of bony osteophytes, to allow proper implant insertion. Use of canal reamers, rasps, and broaches to accomplish this are standard and commonplace in orthopaedic joint arthroplasty practice.

Standard surgical protocol for implanting a bone prosthesis, particularly at a thigh implantation site, is described in Campbell's Operative Orthopaedics, C.V. Mosby Company, 1987.

It is expected that the polymer incorporated in the pores of the prosthesis will provide release of any drug, such as BMP, at the bone-prosthesis interface for at least six weeks, and up to four months.

EXAMPLE 6

Comparative Drug Release from PLA/PGA Copolymer Containing Trypsin Inhibitor or Bone Morphogenetic Protein The present example illustrates the utility of the present invention in providing the protracted release of pharmacologically active agents, such as BMP, from the surface of a prosthetic device impregnated with a polymer matrix. The present study is proposed to demonstrate that mixture of a protein, such as TI or BMP, in a biodegradable polymer will not preclude the release of the protein drug or result only in release of polymer breakdown products.

Materials and Methods

Implants of a copolymer of 50% PLA/50% PGA were prepared as described in example 1 and mixed with 15 mg trypsin inhibitor (Sigma).

Another polymer solution of 50% PLA/50%PGA was mixed with a 15 mg bone morphogenetic protein (BMP) so as to achieve a concentration of 15 mg BMP in the polymer.

The implants were subjected to hydrolytic degradation in phosphate buffered saline at 37° C. The release of protein was monitored using a Micro BCA assay. The results (FIG. 3) indicate similar release characteristics for BMP and TI from a polymer.

Proposed In-Vivo Study

The biomaterial specimens will be degreased using Micro® laboratory cleaning solution, and then ultrasonically cleaned in acetone, methanol and distilled water. The specimens will be sterilized by autoclaving at 140° C. for 90 minutes. Next, the polymer and BMP mixture will be incorporated in the pores of a porous implantable device under sterile conditions. The specimens will then be stored in sterile bags until implantation.

Animal Model

The animal model to be used in this study will be based on a model of endosteal bone healing developed for examining primary mineralization (Bab et al. (1985); Amir et al. (1989); Anse et al. (1969)). Recently this model was adapted for the study of implants (Schwartz et al. (1991)). The minimum size of the specimen required for mechanical testing necessitates the use of rabbits.

Surgical Procedure

For each animal, an infrapatellar incision will be performed to achieve access to the proximal aspect of the right tibial bone under general anesthesia. This will be followed by penetration of the frontal aspect of the bone with a saline cooled dental burr using 20,000 RPM. The bone marrow will then be evacuated by repeated washings with saline introduced into the intrabony space by a cannula. Following ablation, individual biomaterial implants will be introduced into the tibial intramedullary space through the previously mentioned portal. The skin will then be sutured and the animals will be allowed to resume normal weight bearing activities.

Rabbit Model

A total of 72 mature male (approximately 3 kilograms) New Zealand rabbits will be used for the study. The animals will be divided into 2 groups of 36 animals each, corresponding to the two biomaterials. Each group will further be divided into 3 subgroups of 12 animals each, corresponding to the following three implant conditions: (i) Biomaterial with BMP and polymer; (ii) Biomaterial with polymer; (iii) Biomaterial only. Implants of size 3×3×15 mm will be placed intramedullary in the tibia of these animals. Six animals from each subgroup will be sacrificed at days 28 and 56. The specimens will be explanted by bilateral tibial excisions, stripped of all soft tissue and frozen until the time for testing.

Mechanical Testing

The bone-biomaterial specimens retrieved from the rabbit model will be subjected to transverse cuts using a saw with a diamond blade under constant flow of saline, to yield two 1 mm thick specimens for histology and atomic force microscopy. The remaining portion of the specimen will be cleaned and polished so that only a 1 mm thick layer of bone remains attached to one face (approximately 3×10 mm) of the biomaterial implant. All other faces of the implant will be stripped clean. Next, using Hysol Aerospace epoxy, support blocks fabricated from the same material as the specimen will be affixed to the bone and biomaterial. With the help of a dissecting microscope, a Teflon® coated razor blade will then be used to introduce a small, sharp notch at the front end of the bone-biomaterial interface. This notch will serve as a stress concentrator for initiating a crack as required for the test. The specimens will be tested on an Instron tensile testing machine as described under Specific Aim One.

Histopathologic Analysis

Following 48 hours of fixation in 10 percent neutral buffered formalin, the histology specimens will be processed for sectioning in methyl-methacrylate (Fisher Sci., Houston, Tex.) for analysis of the bone-biomaterial interface. These specimens will be sectioned on a diamond saw, ground, and then stained with Toludine Blue, and Massons trichrome as modified by Goldner. Sections considered representative of each specimen will be analyzed histomorphometrically for standard criteria using a Bioquant IV image analysis system. Specific histomorphometric variables are listed in Table 2.

TABLE 2

| Variable | Description |
| --- | --- |
| Cancellous bone | The percent of sample which is composed of cancellous tissue. |
| Collagen | The percent of sample which is composed of collagen and fibrous connective tissue. |
| Bone volume | Percent of cancellous bone and marrow space that is calcified matrix and osteoid. |
| Lamellar bone | The percent of the bone volume which is lamellar as opposed to woven. |
| Osteoclast number | Total number of osteoclasts per histologic section. |
| Osteoblast surface | Percent of trabecular surface lined by phenotypic osteoblasts. |
| Total sample area | Area of histologic section in $mm^2$. |
| Total bion-biomaterial interface | Total bone-biomaterial interface area expressed as a percent of the section area. |
| Total number of implant/bone intersects per slide | The number of Ziess integration plate intersections with bone-biomaterial interface per slide. |

Statistical Analysis

All measurements will be compiled in tables as means and standard deviations. The three main sources of variance in the percent of bone ingrowth and the strength of the bone-biomaterial interfacial bond will be the biomaterial type, the implant condition, and the duration of implantation. A 3-way ANOVA will be performed to test for the effects of these sources, as well as all associated interactions. Depending on the significance of interaction terms, the model will be reduced for further interpretation. For example, if the 3-factor interaction term is not significant but the 2-factor interaction between biomaterial type and the implant condition is significant, then comparisons by T-test would be made between types of biomaterial within types of implant conditions. Also, comparisons by 1-way ANOVA with SNK would be made among types of implant conditions within biomaterial types. Main effects and group comparisons will be considered significant at the 0.05 level, while interaction terms will be considered significant at the 0.15 level. Differences in the slopes of the stress-strains curves will also by analyzed.

EXAMPLE 7

Comparison of Protein Release from Implant with and without Polymer

The present example is provided to demonstrate the differences in protein release from a porous implant impregnated with a protein compared to protein release from a device impregnated with a protein-biodegradable polymer combination.

Materials and Methods 15 mg of trypsin inhibitor (TI) was dissolved in 100 μl of deionized water and poured into the pores of the implant. The implant was covered and allowed to stand for 24 hours at room temperature to evaporate the water.

Protein-polymer combination 0.75 gms of a 50:50% PLA:PGA was dissolved in 5 ml of acetone. A solution of 15 mg TI in 100 μl water was added to the polymer solution which was then poured into the pores of the implant. The implant was then covered and allowed to stand at room temperature until the water and acetone evaporated.

Elution Test

Each implant was immersed in 200 ml phosphate buffered saline (PBS). Every 24 hours a sample of PBS was removed and analyzed for total protein content using a microBCA assays.

Results

The data clearly indicates that over the 96 hours tested, the release of protein from the device treated with the polymer-protein combination was more controlled compared to the release of protein from the device treated with protein alone (not in polymer).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Remingtons Pharmaceutical Sciences, 18th edition (1990), Mack Publishing Company.
2. The Merck Index, 11th edition (1989), Merck & Co., Inc. publishers, Rahway, N.J.
3. Collier et al., "Macroscopic and Microscopic Evidence of Prosthetic Fixation with Porous-Coated Materials', *Clinical Orthopaedics and Related Research,* 235:173–180, 1988.
4. Jasen et al., "Histologic Evaluation of the Osseous Adaptation to Titanium and Hydroxyapatite-Coated Titanium Implants," *J. Biomed. Mater. Res.,* 25:973–989, 1991.
5. Buser et al., "Influence of Surface Characteristics on Bone Integration of Titanium Implants. A Histomorphometric Study in Miniature Pigs," *J. Biomed. Mater. Res.,* 25:889–902, 1991.
6. Albrektsson and Hansson, "An Ultrastructural Characterization of the Interface Between Bone and Sputtered Titanium or Stainless Steel Surfaces," *Biomaterials,* 7:201–205, 1986.

7. Hulbert et al., "Attachment of Prostheses to the Musculoskeletal System by Tissue Ingrowth and Mechanical Interlocking," *J. Biomed. Mater. Res.,* 4:1–12, 1973.
8. Cameron et al., "The Rate of Bone Ingrowth into Porous Metal," *J. Biomed. Mater. Res.,* 10:295-302, 1976.
9. Collier et al., "Bone Ingrowth into Dynamically Loaded Porous-Coated Intramedullary Nails," *J. Biomed. Mater. Res.,* 7:485–488, 1976.
10. Bobyn et al., "The Optimum Pore Size for the Fixation of Porous-Surfaced Metal Implants by the Ingrowth of Bone," *Clin. Orthop.,* 150:263–270, 1980.
11. Cook et al., "Interface Mechanics and Bone Growth into Porous Co-Cr-Mo alloy Implants," *Clinical Orthopaedics and Related Research,* 193:271–280, 1985.
12. ohgushi et al., "Bone Formation Process in Porous Calcium Carbonate and Hydroxyapatite," *J. Biomed. Mater.,* 26:885–895, 1992.
13. Miller et al. "The Induction of Bone by an Osteogenic Protein and the Conducting of Bone by Porous Hydroxyapate: A Laboratory Study in the Rabbit," *Plas. Reconstr. Surg.,* 87:87–95, 1991.
14. Aldinger et al., "Bone Morphogenetic Protein: A Review," *International Orthop. (SICOT),* 15:169–177, 1991.
15. Urist et al., "Osteogenic Competence," *Clin. Orthop.,* 64:194–220, 1969.
16. Urist, *Instr. Course Lecture,* 25:1–26, 1976.
17. Wlodarski and Reddi, "Importance of Skeletal Muscle Environment for Ectopic Bone Induction in Mice," *Folia Biol.,* 34:425–434, 1986.
18. Syftestad and Urist, "Bone Aging," *Clin. Orthop.,* 162:288–297, 1982.
19. Takagi and Urist, "The Reaction of the Dura to bone morphogenetic protein (BMP) in repair of Skull Defects," *Ann. Surg.,* 196:301–311, 1982.
20. Sato and Urist, "Induced Regeneration of Calvaria by Bone Morphogenetic Protein (BMP) in Dogs," *Clin. Orthop.,* 227:265–268, 1988.
21. Lindholm et al., "Bovine Bone Morphogenetic Protein (bBMP) Induced Repair of Skull Trephine Defects in Sheep," *Clin. Orthop.,* 227:265–268, 1988.
22. Ferguson et al., "Bovine Bone Morphogenetic Protein (bBMP) Fraction Induced Repair of Craniotomy Defects in the Rhesus Monkey," *Clin. Orthop.,* 219:251–258, 1987.
23. Mizutani and Urist, "The Nature of Bone Morphogenetic Protein (BMP) Fraction Derived from Bovine Bone Matrix Gelatin," *Clin. Orthop.,* 171:213–223, 1982.
24. D'Alessandro et al., "Purification, Characterization and Activity of Recombinant Human BMP-5," *J. Cell. Biochem.,* S15F:166, 1991.
25. Lee et al. (1994), Journal of Biomedical Materials Research, 28:1149–1156.
26. Lind et al. (Feb. 15–18, 1993), 39th Annual Meeting, Orthopaedic research Society, San Francisco, Calif.
27. Sporn, M. B. (1990), Handbook of Exp. Pharm. Peptide Growth Factors, Vol. 1, New York.
28. Joyce, ME. (1990), J. Cell Biol; 110:2187–2207.
29. Noda, M. (1989), Endocrinology, 124:2991–2994. Beck, S. L. (1991), J. Bons Min. Res., 6:1257–1265.

What is claimed is:

1. A metallic press fit prosthetic device comprising at least one porous tissue mating surface on said metallic press fit prosthetic device having interstitial spaces impregnated with a polymer selected from a group consisting of PLA, PGA, and PLA-PGA copolymer, said polymer having a molecular weight of about 40 to 100,000 kDa and said polymer further containing a pharmacologically active substance, wherein release of said substance at the surface is controlled over a therapeutically effective period of time, when said device is implanted in a patient.

2. The prosthetic device of claim 1 wherein the tissue-mating surface is a bone-mating surface.

3. The prosthetic device of claim 1 wherein the PLA-PGA copolymer is a copolymer of about 50% polylactic and about 50% polyglycolic acid.

4. The prosthetic device of claim 1 wherein the device is a total joint prosthesis.

5. The prosthetic device of claim 1 wherein the device is a hip, knee, shoulder, elbow, ankle, wrist, hand, finger joint, temporal mandibular joint, dental implant, or acetabular cup implant prosthesis.

6. The prosthetic device of claim 5 wherein the device is a knee prosthesis.

7. The prosthetic device of claim 1 wherein the pharmacologically active substance is an antibiotic.

8. The prosthetic device of claim 2 wherein the porous bone-mating surface comprises a cobalt chrome alloy, a titanium alloy, or stainless steel.

9. A method of delivering a pharmacologically active agent comprising implanting into an animal a metallic press-fit prosthetic device comprising at least one microporous tissue mating surface having interstitial spaces impregnated with a polymer selected from the group consisting of PLA, PGA, and PLA-PGA copolymer, said polymer having a molecular weight of about 40 to 100,000 kDa, said polymer further comprising a pharmacologically active agent.

10. The method of claim 9 wherein the PLA-PGA copolymer is a co-polymer of about 50% polylactic acid and about 50% polyglycolic acid.

* * * * *